United States Patent [19]

Kurono et al.

[11] Patent Number: 5,037,981
[45] Date of Patent: Aug. 6, 1991

[54] INTERMEDIATES FOR SYNTHESIZING BH$_4$ AND ITS DERIVATIVES

[75] Inventors: Masayasu Kurono, Mie; Takehiko Suzuki; Tomio Ogasawara, both of Kasugai; Nobuko Ohishi, Gifu; Kunio Yagi, Nagoya, all of Japan

[73] Assignee: Kabushiki Kaisha Vitamin Kenkyuso, Gifu, Japan

[21] Appl. No.: 515,962

[22] Filed: Apr. 27, 1990

Related U.S. Application Data

[62] Division of Ser. No. 277,109, Nov. 29, 1988, Pat. No. 4,937,342.

[30] Foreign Application Priority Data

Nov. 30, 1987 [JP] Japan ................................ 62-299977
Nov. 30, 1987 [JP] Japan ................................ 62-299978
Nov. 30, 1987 [JP] Japan ................................ 62-299979
Nov. 30, 1987 [JP] Japan ................................ 62-299980
Jun. 22, 1988 [JP] Japan ................................ 63-152217

[51] Int. Cl.$^5$ .......................................... C07D 239/47
[52] U.S. Cl. .................................................. 544/320
[58] Field of Search ........................................ 544/320

[56] References Cited

U.S. PATENT DOCUMENTS 4,939,252 7/1990 Schwartz ........................... 544/320

OTHER PUBLICATIONS

Chemistry of Organic Synthesis, vol. 46, No. 6 (1988), p. 570.

*Primary Examiner*—Donald G. Daus
*Attorney, Agent, or Firm*—Armstrong, Nikaido, Marmelstein, Kubovcik & Murray

[57] ABSTRACT

The present invention relates to intermediates for synthesizing BH$_4$ and derivatives thereof. The intermediates are shown as follows;

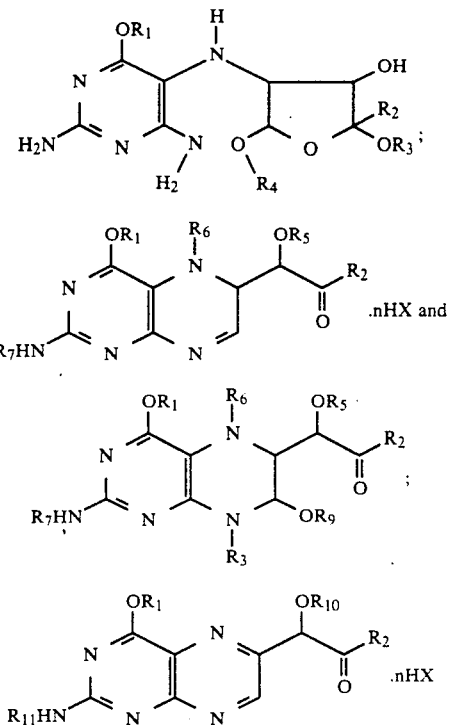

wherein R$_1$ is a hydrogen atom, alkyl, aralkyl, or aryl group; R$_2$ is an alkyl, hydroxyalkyl, or polyhydroxyalkyl group; R$_3$ and R$_4$ are the same or different and represent alkyl, aralkyl, or aryl group; R$_5$, R$_6$, R$_7$, and R$_8$ are the same or different and represent a hydrogen atom or acyl group; R$_9$ is an alkyl, aralkyl, or aryl group; R$_{10}$ and R$_{11}$ are the same or different and represent a hydrogen atom or acyl group; n is an integer of 5 or less; and HX is an acid. The invention also relates to a process for the preparation of L-biopterin.

1 Claim, No Drawings

INTERMEDIATES FOR SYNTHESIZING BH₄ AND ITS DERIVATIVES

This is a division of application Ser. No. 277,109, filed Nov. 29, 1988, now U.S. Pat. No. 4,937,342.

BACKGROUND OF THE INVENTION

1. Field of the Invention

The present invention relates to intermediates for synthesizing BH₄ and its derivatives, as well as to a process for the preparation of L-biopterin.

2. Related Arts

The compound BH₄, namely, 5,6,7,8-tetrahydro-L-erythrobiopterin, is one of the coenzymes of aromatic amino acid hydroxylase, is an indispensable compound for biosynthesis of dopamine, noradrenalin, adrenaline, and melatonin, and is reprsented by the following formula:

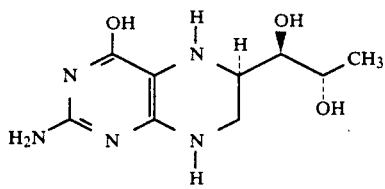
(II)

A deficiency of BH₄ causes serious neurological disorders like atypical phenylketonuria and Parkinsonism: and recently, it has been found that symptoms due to such diseases can be remarkably improved by administration of BH₄. Further, it has been recognized that BH₄ is effective for curing infantile autism and depressions.

Since BH₄ has such useful pharmacological activities, various studies have been made for the synthesis thereof, and are referenced as follows: E. L. Patterson et al. "J. Am. Chem. Soc." Vol. 78, page 5868 (1956); H. Rembold et al. "Chem. Ber." Vol. 96, page 1395 (1963); E. C. Taylor et al. "J. Am. Chem. Soc." Vol. 98, page 2301 (1976); M. Viscontini et al. "Helv. Chim. Acta" Vol. 52, page 1225 (1969); ibid., Vol. 55, page 574 (1972); ibid., Vol. 60, page 211 (1977); ibid., Vol 62, page 2577 (1979); K. J. M. Andrews et al. "J. Chem. Soc." (c), page 928 (1696); S. Matsuura et al. "Bull. Chem. Soc. Jpn. " Vol. 48, page 3767(1975); ibid., Vol. 52, page 181 (1979); "Chem. Lett." page 735 (1984); Jap. Pat. No. 59-21685(A); ibid., 59-82091(A); and ibid., 60-204786(A).

Each of the conventional processes for preparing BH₄ has several drawbacks in that an expensive saccharide is required as starting material to provide the asymmetric carbon atom at its side-chain, that yield and purity will become low due to multi-reaction steps, through unstable intermediates that require troublesome treatment operations, and that it requires troublesome purification procedures. Therefore, the conventional processes are unsuitable for industrial production of the compound and its derivatives.

SUMMARY OF THE INVENTION

The present inventors have energetically worked to develop a process for preparing BH₄, one which can be applied for a commercial and convenient production thereof, by taking the following points into consideration:

a) The starting material is available at reasonable cost,
b) The number of synthetic steps can be made minimum,
c) Good yield can be attained, and
d) If possible, it can be applied for synthesizing compounds analogous to BH₄.

As a result, they have found that a tetrahydrofuranylpyrimidine derivative of the formula

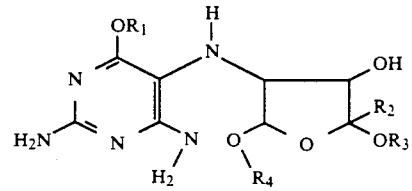
(I)

wherein $R_1$ is a hydrogen atom, alkyl, aralkyl, or aryl group; $R_2$ is an alkyl, hydroxyalkyl, or polyhydroxyalkyl group; $R_3$ and $R_4$ are the same or different and represent alkyl, aralkyl or aryl group, is suitable as an intermediate for synthesizing BH₄ and analogous compounds thereof to open the way for the present invention.

The following are steps for synthesizing the tetrahydrofuranylpyrimidine derivatives shown by said Formula I as well as BH₄ and its analogous compounds:

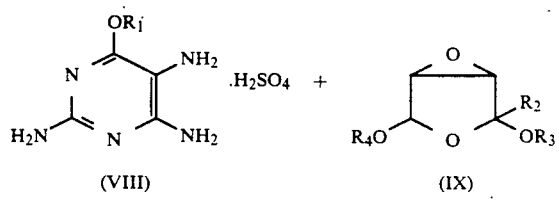

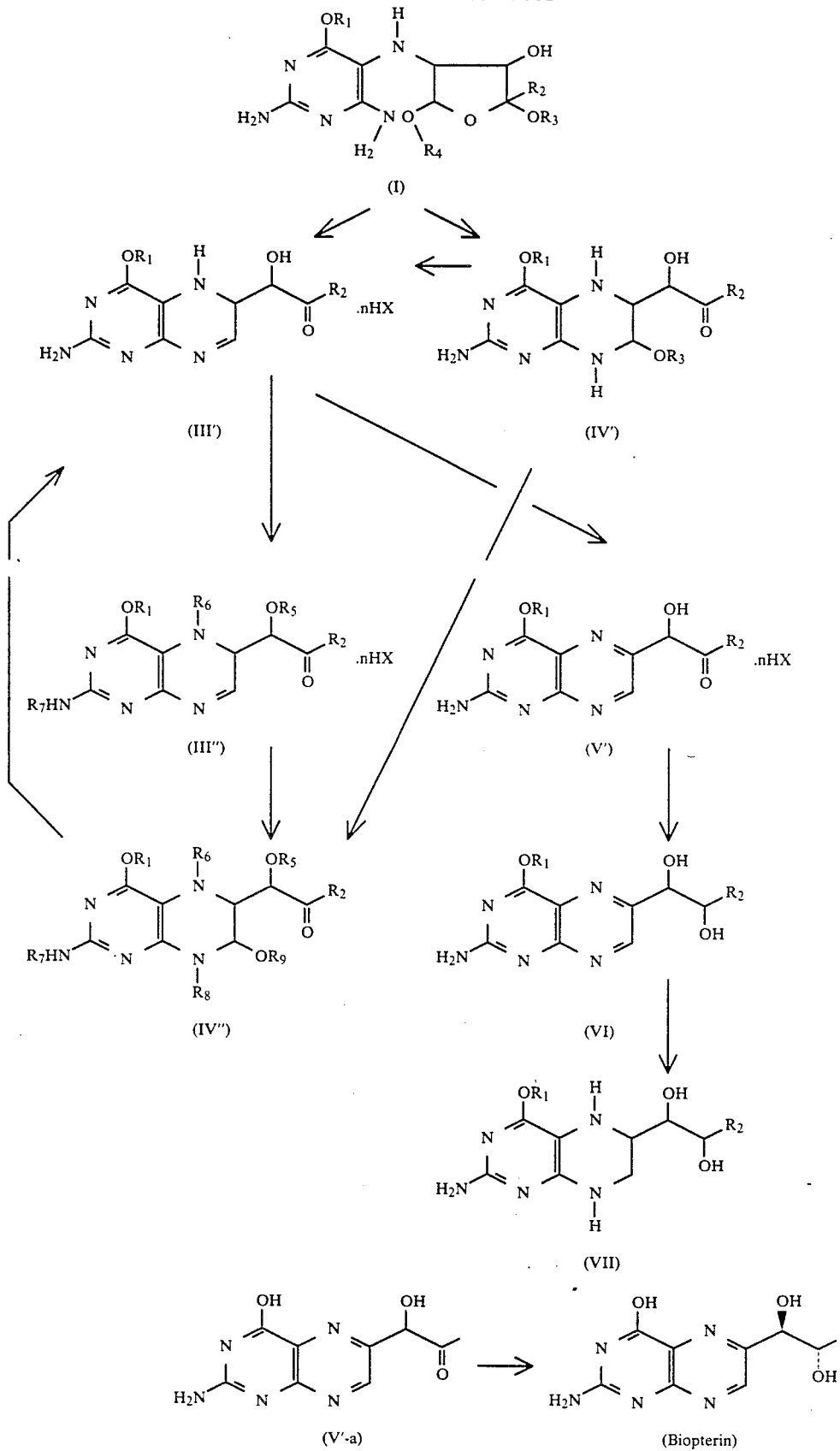
wherein $R_1$, $R_2$, $R_3$, and $R_4$ have the meanings as already stated; $R_5$, $R_6$, $R_7$, and $R_8$ are the same or different and represent a hydrogen atom or acyl group; $R_9$ is an alkyl, aralkyl or aryl group; n is an integer of 5 or less; and HX is an acid.

In connection with the compounds, the definitions of each substituent shall generally be given as follows: The alkyl group may be of methyl, ethyl, propyl, butyl, pentyl, hexyl group, isomers thereof or the like. The aralkyl group may be of benzyl, xylyl, phenethyl group or the like. The aryl group may be of phenyl, tolyl, anisoyl, naphthyl group or the like. The hyroxyalkyl group may be of hydroxymethyl, hydroxyethyl, hydroxypropyl group or the like. The polyhydroxyalkyl group may be of 1,2-dihydroxyethyl, 1,2-dihydroxypropyl, 2,3-dihydroxypropyl, 1,2,3-trihydroxypropyl group or the like.

The tetrahydrofuranylpyrimidine derivative (I) can be prepared by reacting 2,4,5-triaminopyrimidine derivative (VIII) with an epoxy-tetrahydrofuran derivative (IX).

The tetrahydrofuranylpyrimidine derivative (I) can be converted into dihydropteridine derivative (III') or tetrahydropteridine derivative (IV') by hydrolyzing its acetal portion with an acid, and by ring closing at the amino group portion. The dihydropteridine derivative The pteridine derivative (V') can be converted into biopterin derivative (VI) by reducing the carbonyl group in its side-chain. This reduction can be carried out with the use of sepiapterin reductase in the manner as described by S. Katoh et al. "Biochem. Biophys. Res. Commun." Vol. 118, page 859 (1984), or with use of a conventional reducing reagent. In this connection, a conversion from the biopterin derivative (VI) to tetrahydrobiopterin derivative (VII) has already been reported in various papers, for instance, S. Matsuura et al. "Chem. Lett." page 735 (1984), and Jap. Pat. No. 59-21685 (A), 59-82091(A) and 60-204786(A).

According to the invention, L-biopterin can be prepared by treating biopterin derivative (V'-a), wherein $R_1$ [of (v')] is a hydrogen atom, and $R_2$ is a methyl group, with sepiapterin redutase. In connection with this, please note that the reduction of 2-amino-4-hydroxy-6-(1'-hydroxy-2'-oxopropyl)pteridine (V'-a) shall, in general, produce four compounds; but according to the invention, L-biopterin (compound 1) can only and unexpectedly be formed with a stereospecificity.

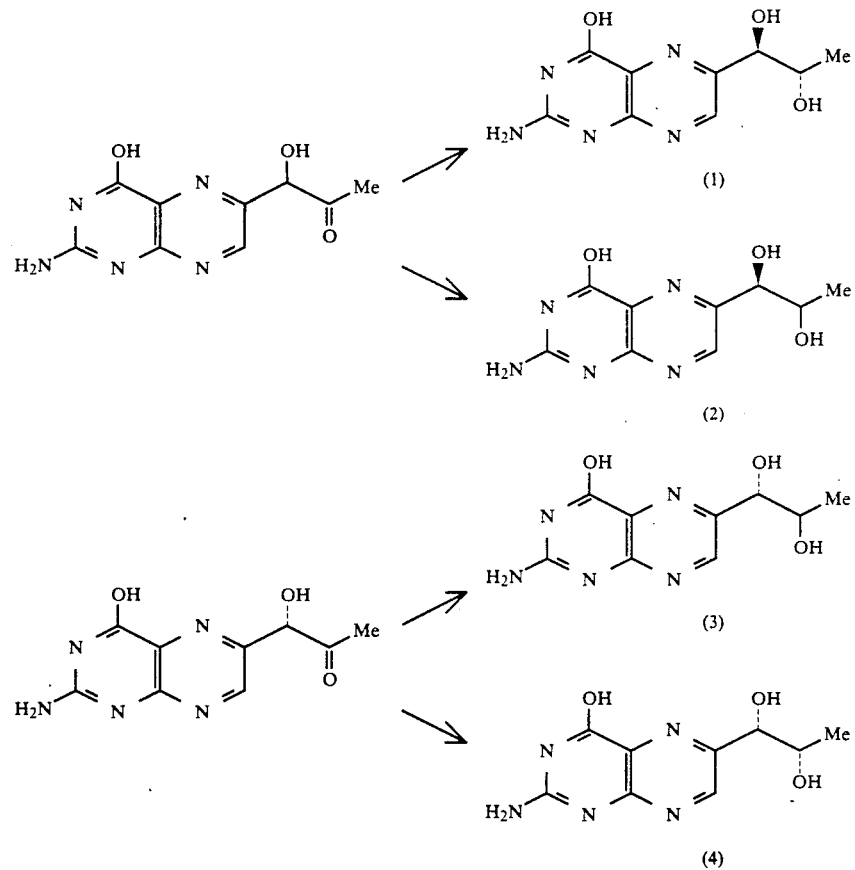

(III') can be converted into pteridine derivative (V') by oxidizing its pteridine ring, or into acyl-dihydropteridine derivative (III'') through an acylation. The acyl-dihydropteridine derivative (III'') can easily be changed by treating with an alcohol into acyl-tetrahydropteridine derivative (IV''') which can, in turn, be converted again into the dihydropteridine derivative (III') by treating the same with an acid. While, the tetrahydropteridine derivative (IV') can be transformed into dihydropteridine derivative (III') by treating the same with an acid, or into acyltetrahydropteridine derivative (IV'') through an acylation thereof.

In the above synthetic procedures, $BH_4$ can be prepared as the final product (VII), when $R_1$ is a hydrogen atom and $R_2$ is a methyl group. Neopterin is also synthesized by this prodedure, when $R_1$ is a hydrogen atom and $R_2$ is a hydroxymethyl group. Therefore, $BH_4$ and its analogous compounds can be synthesized easily and at a reasonable cost, when the compounds according to the invention are utilized as an intermediate therefor.

PREFERRED EMBODIMENTS OF THE INVENTION

The invention will now be further explained in more detail with reference to Examples.

EXAMPLE 1 a) 2,5-Dihydro-2,5-dimethoxy-2-methylfuran

To a mixture of 2-methylfuran (123 g, 1.50 mol), sodium carbonate (318 g, 3.00 mol) and methanol (2180 ml) cooled at −75° C. under stirring in a dry ice/acetone bath, dichloromethane (87.9 ml) containing bromine (240 g, 1.50 mol) was added dropwise over 4 hours.

After completion of the addition, the reaction mixture was removed from the bath and allowed to come to room temperature; it was then filtered to remove sodium bromide. Saturated sodium chloride solution was added to the filtrate, which was extracted with dichloromethane 3 times. The combined dichloromethane layer was washed twice with saturated sodium chloride solution and dried over anhydrous sodium sulfate. The resulting solution was concentrated in a water bath kept at 50° C. or less and distilled in vacuo to afford 171 g (79.1%) of the titled compound.

Boiling point: 54° C. ($bp_{14}$).

$^1$H—NMR spectrum ($CDCl_3$, δ ppm):
1.51, 1.57 (3H, s×2, —$CH_3$)
3.12, 3.20 (3H, s×2, —$OCH_3$)
3.43, 3.50 (3H, s×2, —$OCH_3$)
5.48, 5.76 (1H, proton at 5-position)
5.96 (2H, m, olefinic proton)
Silica gel TLC: Rf=0.53, 0.59 (hexane: ethyl acetate=5:1)

b) 3,4-Epoxy-2,5-dimethoxy-2-methyltetrahydrofuran

To a mixture of 2,5-dihydro-2,5-dimethoxy-2-methylfuran (21.6 g, 150 mmol), benzonitrile (17.0 g, 165 mmol), and methanol (40 ml) heated at 40° C., 31% aqueous solution of hydrogen peroxide (11.0 g, 100 mmol) was added dropwise over 2.5 hours, while maintaining pH in a range of 7.50 to 8.00 by addition of an aqueous solution of sodium hydroxide. Then the mixture was further reacted for 17.5 hours, while maintaining the temperature at 60° C. and pH in the range of 7.50 to 8.00.

After confirmation of the exhaustion of the peroxide by iodometry, the reaction mixture was cooled to room temperature, 60 ml of water was added to it, and it was extracted three times with chloroform. After the extract was washed with water three times, pentane was added to the chloroform layer to remove benzamide. The resulting filtrate was concentrated to obtain a crude product (30.7 g), which was subjected to silica gel chromatography (elution solvent, hexane: ethyl acetate=6:1), so as to afford 2.21 g (9.2%) of the titled compound.

$^1$H—NMR spectrum ($CDCl_3$ δ ppm):
1.51 (3H, s, —$CH_3$)
3.33 (3H, s, —$OCH_3$)
3.47 (1H, d, J=2.7Hz, proton at 3-position)
3.52 (3H, s, —$OCH_3$)
3.67 (1H, br.d, J=2.7 Hz, proton at 4-position)
5.10 (1H, br.s, proton at 5-position).
Silica gel TLC: Rf=0.47 (hexane: ethyl acetate=2:1), c) 2,4-Diamino-6-hydroxy-5-[4'-(3'-hydroxy-2',5'-dimethoxy-2'-methyltetrahydrofuranyl)]pyrimidine To a suspension of 2,4,5-triamino-6-hydroxypyrimidine sufate (8.66 g, 36.2 mmol) in ethanol (18 ml), sodium carbonate (7.69 g, 72.5 mmol) dissolved in distilled water (72.5 ml) was added. After completion of bubbling with carbon dioxide gas, 3,4-epoxy-2,5-dimethoxy-2-methyltetrahydrofuran (2.90 g, 18.1 mmol) dissolved in ethanol (18.3 ml) was added, and the resulting mixture was heated to 100° C. under nitrogen atmosphere to react for 69 hours.

After the mixture was cooled to room temperature, methanol (50 ml) was added to it and solids were removed by filtration. After concentration of the filtrate, methanol (50 ml) was added and then insoluble matter was filtered off. The resulting filtrate was concentrated to obtain a crude product which was, in turn, subjected to latrobeads column chromatography (elution solvent, methanol) to afford 2.94 g (53.9%) of the titled compound.

$^1$H—NMR spectrum (pyridine—$D_5$, δ ppm): 1.74 (3H, s, —$CH_3$) 3.44 (3H, s, —$OCH_3$) 3.49 (3H, s, —$OCH_3$) 3.81 (1H, m, proton at 4'-position) 4.71 (1H, br.d, J=6 Hz, proton at 3'-position) 5.38 (1H, br.d, J=5 Hz, proton at 5'-position).

$^{13}$C—NMR spectrum (DMSO—$D_6$, δ ppm): 19.4, 48.1, 55.2, 70.1, 77.2, 98.1, 107.0, 108.0, 152.2 160.9, 161.4.

IR spectrum (KBr, $cm^{-1}$): 3328, 1588.
MS spectrum (El): 301($M^+$), 269.
Silica gel TLC: Rf=0.27 (chloroform: methanol=5:1).

EXAMPLE 2

2-Amino-4-hydroxy-7-methoxy-6-(1'-hydroxy-2'-oxopropyl)-5,6,7,8-tetrahydropteridine To 2,4-diamino-6-hydroxy-5-[4'-(3'-hydroxy-2',5'-dimethoxy-2'-methyltetrahydrofuranyl)]pyrimidine (70 mg, 0.232 mmol) obtained by the process described in Example 1, acetic acid (3.0 ml) was added, and the mixture was stirred at 50° C. for 20 minutes. After being cooled to room temperature, the reaction mixture was dried in vacuo to obtain a crude product which was, in turn, subjected to silica gel thin-layer chromatography (developing solvent, chloroform: methanol=5:1) to afford 17.6 mg (28.2%) of the titled compound.

$^1$H—NMR spectrum (DMSO—$D_6$, δ ppm): 2.22 (3H, s, —$CH_3$) 3.03 (1H, m, proton at 6-position) 3.49 (3H, s, —$OCH_3$) 4.13 (1H, br.t, proton at 1'-position) 4.88 (1H, d, J=6 Hz, proton at 7-position) 5.69 (1H,br.d, J=6 Hz, hydroxy proton at 1'-position).

$^{13}$C—NMR spectrum (DMSO—$D_6$, δ ppm): 26.6, 55.6, 55.7, 74.4, 96.9, 98.5, 155.9, 157.7, 158.1 210.4.
MS spectrum (El): 269($M^+$), 196.
Silica gel TLC: Rf=0.48 (chloroform:methanol=5:1).

EXAMPLE 3

2-Acetamido-5-acetyl-4-hydroxy-7-methoxy-6-(1'-hydroxy-2'-oxopropyl)-5,6,7,8-tetrahydropteridine To 2,4-diamino-6-hydroxy-5-[4'-(3'-hydroxy-2',5'-dimethoxy-2'-methyltetrahydrofuranyl)]pyrimidine (220 mg, 0.730 mmol) obtained by the process described in Example 1, 6N hydrochloric acid (2.20 ml) was added, and the mixture was stirred for 10 minutes at room temperature and then concentrated in vacuo. After the concentrate was cooled on ice, acetic anhydride (3.50 ml) and pyridine (3.50 ml) were added and allowed to react for 1 hour at room temperature under stirring. After removal of insoluble matter by filtration, the filtrate was poured into ether (60 ml), and the semi-solid material that appeared was collected by decantation. The material was then washed three times with ether and dried in vacuo. To the dried material, methanol (7 ml) was added and allowed to react for 30 minutes at room temperature under stirring. The reaction mixture was subjected to silica gel thin-layer chromatography (developing solvent, chloroform:methanol=5:1) to afford 73.9 mg (28.8%) of the titled compound.

$^1$H—NMR spectrum (DMSO—D$_6$, δ ppm): 1.96, 1.99, 2.14 (3H×3, s×3, CH$_3$CO×2, —CH$_3$) 3.19 (3H, s, —OCH$_3$) 4.58 (1H, br.d, J=4.5 Hz, proton at 7-position) 4.86 (1H, d, J=7.3 Hz, proton at 1'-position) 5.22 (1H, br.d, J=7.3 Hz, proton at 6-position) 7.91 (1H, br.d, J=4.5 Hz, proton at 8-position).

$^{13}$C—NMR spectrum (DMSO—D$_6$, δ ppm): 20.2, 21.7, 26.5, 47.5, 53.5, 74.7, 81.9, 92.7, 153.0 153.3, 157.4, 169.5, 171.0, 204.1.

IR spectrum (KBr, cm$^{-1}$): 3344, 1710, 1616.

Silica gel TLC: Rf=0.27 (chloroform: methanol=5:1).

EXAMPLE 4

2-Acetamido-4-hydroxy-7-methoxy-6-(1'-acetoxy-2'-oxopropyl)-5,6,7,8-tetrahydropteridine To 2,4-diamino-6-hydroxy-5-[4'-(3'-hydroxy-2',5'-dimethoxy-2'-methyltetrahydrofuranyl)]pyrimidine (150 mg, 0.498 mmol) obtained by the process described in Example 1, acetic acid (1.5 ml) was added, and the mixture was stirred for 20 minutes at 50° C. After being cooled to room temperature, the reaction mixture was dried in vacuo. A part of the dried substance was taken and subjected to $^1$H—NMR spectroscopy to confirm the formation of 2-amino-4-hydroxy-7-methoxy-6-(1'-hydroxy-2'-oxopropyl)-5,6,7,8-tetrahydropteridine (see Example 2).

After the other part was ice-cooled, acetic anhydride (2.5 ml) and pyridine (2.5 ml) were added, and the mixture was stirred for 1 hour at room temperature: then ether (50 ml) was added. The resulting solid material was collected filtration and washed with ether to obtain 94.1 mg of a crude product which was subjected to silica gel thin-layer chromatography (developing solvent, chloroform: methanol=5:1) to afford 20.0 mg (11.4%) of the titled compound.

$^1$H—NMR spectrum (DMSO—D$_6$, δ ppm): 2.01, 2.10, 2.17 (3H×3, s×3, CH$_3$CO×2, —CH$_3$) 3.42 (3H, s, —OCH$_3$) 3.83 (1H, m, proton at 6-position) 4.86 (1H, br.d, J=6.8 Hz, proton at 5-position) 5.18 (1H, d, J=2.0 Hz, proton at 7-position) 5.28 (1H, d, J=3.4 Hz, proton at 1'-position).

$^{13}$C—NMR spectrum (DMSO—D$_6$, δ ppm): 20.3, 24.1, 27.0, 52.4, 55.3, 77.7, 96.6, 103.6, 148.3 152.4, 155.0, 168.9, 169.6, 203.9.

MS spectrum (El): 353(M$^+$).

Silica gel TLC: Rf=0.45 (chloroform: methanol=5:1).

EXAMPLE 5

2-Amino-4-hydroxy-6-(1'-hydroxy-2'-oxopropyl)-5,6-dihydropteridine

To 2,4-diamino-6-hydroxy-5-[4'-(3'-hydroxy-2',5'-dimethoxy-2'-methyltetrahydrofuranyl)]pyrimidine (10 mg, 0.033 mmol) obtained by the process described in Example 1, 6N hydrochloric acid (100 μl) was added, and the mixture was stirred for 10 minutes at room temperature and immediately concentrated in vacuo to afford 9 mg of the titled compound as crude product.

This substance exsits in the following chemical equilibrium in hydrochloric acid solution:

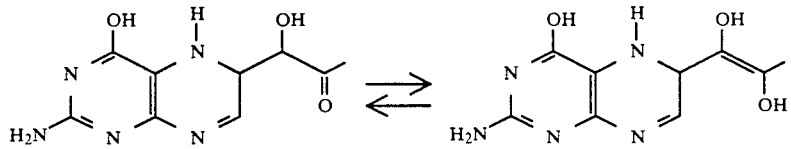

$^1$H—NMR spectrum (20% DCl, δ ppm): 2.51, 2.54 (3H, s×2, —CH$_3$) 4.17, 4.37 (1H, br.d, br.s, J=7 Hz, proton at 6-position) 4.88 (br.d, J=7 Hz, proton at 1'-position) 5.65, 5.74 (1H, br.s×2, proton at 7-position).

IR spectrum (KBr, cm$^{-1}$): 3260, 1650.

MS spectrum (FAB, positive) 238[(M+H)$^+$], 165.

EXAMPLE 6

2-Amino-4-hydroxy-6-(1'-hydroxy-2'-oxopropyl)-5,6-dihydropteridine

To 2-amino-4-hydroxy-7-methoxy-6-(1'-hydroxy-2'-oxopropyl)-5,6,7,8-tetrahydropteridine (30 mg, 0.10 mmol) obtained by the process described in Example 2, 6N hydrochloric acid (600 μl) was added, and the mixture was stirred for 10 minutes at room temperature and concentrated in vacuo to afford 23 mg of the titled compound as crude product.

Physico-chemical data of this compound were the same as those disclosed in Example 5.

EXAMPLE 7

2-Acetamido-5-acetyl-4-hydroxy-6-(1'-hydroxy-2'-oxopropyl)-5,6-dihydropteridine

To 2,4-diamino-6-hydroxy-5-[4'-(3'-hydroxy-2',5'-dimethoxy-2'-methyltetrahydrofuranyl)]pyrimidine (220 mg, 0.730 mmol) obtained by the process described in Example 1, 6N hydrochloric acid (2.20 ml) was added, and the mixture was stirred for 10 minutes at room temperature and then dried in vacuo. After the material was cooled on ice, acetic anhydride (3.50 ml) and pyridine (3.50 ml) were added to the concentrate and allowed to react for 1 hour under stirring. After insoluble matter was filtered off, the filtrate was poured into ether (60 ml), and the resulting semi-solid material was obtained by decantation, which material was washed three times with ether and dried in vacuo to afford 400 mg of the titled compound as crude product.

$^1$H-NMR spectrum (pyridine-D$_5$, δ ppm): 2.15, 2.34, 2.54 (3H×3, s×3, CH$_3$CO×2, —CH$_3$) 5.62 (1H, d, J=8 Hz, proton at 1'-position) 5.96 (1H, br.s, proton at 7-position) 6.24 (1H, br.d, J=8 Hz, proton at 6-position).

MS spectrum (FAB, positive): 322 [(M+H)+].

EXAMPLE 8

2-Amino-4-hydroxy-6-(1'-hydroxy-2'-oxopropyl)-5,6-dihydropteridine

To 2-acetamido-5-acetyl-4-hydroxy-7-methoxy-6-(1'-hydroxy-2'-oxopropyl)-5,6,7,8-tetrahydropteridine (10 mg, 0.028 mmol) obtained by the process described in Example 3, 6N hydrochloric acid (300 μl) was added, and the mixture was stirred for 6 hours at room temperature and then concentrated in vacuo to afford 6.5 mg of the titled compound as crude product.

This compound gave physico-chemical data the same as those listed in Example 6.

EXAMPLE 9

2-Amino-4-hydroxy-6-(1'-hydroxy-2'-oxopropyl)pteridine

To 2,4-diamino-6-hydroxy-5-[4'-(3'-hydroxy-2',5'-dimethoxy-2'-methyltetrahydrofuranyl)]pyrimidine (200 mg, 0.664 mmol) obtained by the process described in Example 1, 6N hydrochloric acid (2.00 ml) was added, and the mixture was stirred for 10 minutes at room temperature. A part of the reaction mixture was taken, concentrated to dryness in vacuo and checked by $^1$H—NMR spectroscopy to confirm the formation of 2-amino-4-hydroxy-6-(1'-hydroxy-2'-oxopropyl)-5,6-dihydropteridine (see Example 5).

The remaining reaction solution was added to a suspension of iodine (600 mg, 2.36 mmol) in methanol (2.00 ml) and methanol (1.00 ml) was further added thereto.

After the reaction had proceeded for 10 minutes at room temperature, distilled water (5.00 ml) was added. Then neutralization was achieved with sodium carbonate (764 mg, 7.21 mmol), and then distilled water (10 ml) was added to the reaction mixture to obtain a dark brown solid that was collected by filtration. The solids were washed with water followed by methanol and dried in vacuo to afford 99.2 mg (63.5%) of the titled compound, as pale yellow solids.

$^1$H—NMR spectrum (DMSO—D$_6$, δ ppm): 2.18 (3H, s, —OCH$_3$) 5.24 (1H, d, J=6 Hz, proton at 1'-position) 6.33 (1H, d, J=6 Hz, hydroxy proton at 1'-position) 6.96 (2H, br.s, amino proton at 2-position) 8.71 (1H, s, proton at 7-position).

IR spectrum (KBr, cm $^{-1}$): 3248, 1652.

mili-MS spectrum: C$_9$H$_9$N$_5$O$_3$, 235 (M+), 219, 192, 177, 163, 136, 122.

EXAMPLE 10

L-Biopterin

To 2-amino-4-hydroxy-6-(1'-hydroxy-2'-oxopropyl)-pteridine (23.6 mg, 100 μmol) obtained by the process described in Example 9, in distilled water (100 ml), β-nicotinamide adenine dinucleotide phosphate (reduced type) (167 mg) dissolved in 0.2M phosphate buffer (pH 6.4, 100 ml) was added. One unit of sepiapterin reductase from rat erythrocytes partially purified by the method described by Sueoka et al. ["Biochim. Biophys. Acta" Vol. 717, page 265 (1982)] was added to the mixture. The resulting solution was incubated for 5 hours at 30° C. with shaking, ultrafiltered, and freeze dried. The freeze dried material was dissolved in a mixture of 0.1N acetic acid/MeOH (95/5, V/V) and purified by high-performance liquid chromatography using a Develosil ODS column. The solvent was removed from the resulting L-biopterin-containing fractions to obtain a residue which was suspended in a small amount of distilled water and freeze-dried to afford 10.5 mg (44%) of the desired compound, as pale yellow powder. $[\alpha]_D^{25} = -60°$ (c=0.13, 0.1N—HCl).

UV spectrum (0.1N—HCl) $\lambda_{max}$ nm: 210, 247, 320.

$^1$H—NMR spectrum (DMSO—D$_6$, δ ppm): 1.06 (3H, d, J=6 Hz, —CH$_3$) 3.92 (1H, m, 2'—H) 4.44 (1H, dd, J=5 Hz, 5 Hz, 1'—H) 4.69 (1H, d, J=5 Hz, 2'—OH) 5.58 (1H, d, J=5 Hz, 1'—OH) 6.86 (2H, s, 2—NH$_2$) 8.71 (1H, s, 7—H) 11.42 (1H, br.s, 3—NH).

Said value of specific rotation is substantially the same as that reported by B. Green et al. ["Chem. Ber." Vol. 99, page 2162 (1966)], and the values of UV and NMR spectra coincide with those of standard samples.

We claim:

1. A tetrahydrofuranylpyrimidine compound of the formula

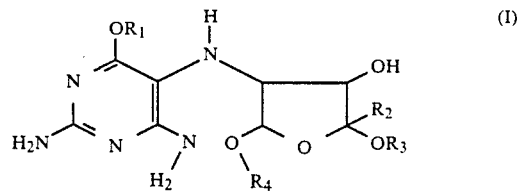

wherein R$_1$ is a hydrogen atom, or a C$_1$-C$_6$ alkyl, benzyl, xylyl, phenethyl, phenyl, tolyl, anisoyl or naphthyl group; R$_2$ is a C$_1$-C$_6$ alkyl, hydroxy C$_1$-C$_3$ alkyl, or polyhydroxy C$_1$-C$_3$ alkyl; R$_3$ and R$_4$ are the same or different and each is a C$_1$-C$_6$ alkyl, benzyl, xylyl, phenethyl, phenyl, tolyl, anisoyl or naphthyl group.

* * * * *

UNITED STATES PATENT AND TRADEMARK OFFICE
CERTIFICATE OF CORRECTION

PATENT NO. : 5,037,981
DATED : August 6, 1991
INVENTOR(S) : Masayasu KURONO et al It is certified that error appears in the above-identified patent and that said Letters Patent is hereby corrected as shown below:

On the title page, Item [75], the third and four inventors should be deleted from the inventorship.

On the title page, Item [57], third compound, "$R_3$" should read -- $R_8$ --.

Signed and Sealed this

Sixth Day of April, 1993

Attest:

STEPHEN G. KUNIN

*Attesting Officer*  Acting Commissioner of Patents and Trademarks